(12) United States Patent
Garab et al.

(10) Patent No.: US 6,856,391 B2
(45) Date of Patent: Feb. 15, 2005

(54) METHOD AND APPARATUS FOR DETERMINING THE POLARIZATION PROPERTIES OF LIGHT EMITTED, REFLECTED OR TRANSMITTED BY A MATERIAL USING A LASER SCANNING MICROSCOPE

(76) Inventors: Gyózó Garab, Dózsa Gy. u. 7, Szeged (HU), H-6720; István Pomozi, Dagály u. 5, Budapest (HU), H-1138; Georg Weiss, St.-Jacob-Str. 22, Jena (DE), 07743; Reinhard Jörgens, Tannweiler-str. 9, Waldstetten (DE), 73550

( * ) Notice: Subject to any disclaimer, the term of this patent is extended or adjusted under 35 U.S.C. 154(b) by 0 days.

(21) Appl. No.: 10/196,593

(22) Filed: Jul. 17, 2002

(65) Prior Publication Data

US 2003/0058442 A1 Mar. 27, 2003

Related U.S. Application Data

(63) Continuation of application No. PCT/HU01/00116, filed on Nov. 16, 2001.

(30) Foreign Application Priority Data

Nov. 17, 2000 (HU) .............................................. 0004571

(51) Int. Cl.[7] ................................................. G01J 4/00
(52) U.S. Cl. ...................... 356/366; 356/368; 356/369; 250/225
(58) Field of Search ......................... 356/369, 364–368, 356/237.2, 630, 236, 631, 632, 231.1–237.6; 250/225, 306, 458.1, 341.3

(56) References Cited

U.S. PATENT DOCUMENTS

| | | | | |
|---|---|---|---|---|
| 4,306,809 A | * | 12/1981 | Azzam ........................ 356/368 |
| 5,257,092 A | | 10/1993 | Noguchi et al. ............ 356/367 |
| 5,389,783 A | * | 2/1995 | Shionoya et al. ........... 250/234 |
| 5,457,536 A | | 10/1995 | Kornfield et al. ........... 356/366 |
| 5,764,363 A | * | 6/1998 | Ooki et al. .................. 356/364 |
| 5,965,874 A | | 10/1999 | Aso et al. .................... 250/225 |
| 6,025,917 A | | 2/2000 | Toyonaga et al. ........... 356/364 |
| 6,097,488 A | | 8/2000 | Grek et al. .................. 356/364 |
| 6,134,011 A | * | 10/2000 | Klein et al. ................. 356/369 |
| 6,175,412 B1 | * | 1/2001 | Drevillon et al. ........... 356/369 |
| 6,356,036 B1 | * | 3/2002 | Zhou ........................... 315/215 |
| 6,384,916 B1 | * | 5/2002 | Furtak et al. ................ 356/369 |
| 6,515,745 B2 | * | 2/2003 | Vurens et al. ............... 356/369 |

FOREIGN PATENT DOCUMENTS

JP 11-095114 4/1999

OTHER PUBLICATIONS

Nielsen P. M. F. et al., "Polarization–sensitive scanned fiber confocal microscope," *Optical Engineering*, vol. 35, No. 11, pp. 3084–3091 (Nov., 1996).

* cited by examiner

*Primary Examiner*—Layla Lauchman
(74) *Attorney, Agent, or Firm*—Morgan, Lewis & Bockius LLP

(57) ABSTRACT

The invention relates to a method and apparatus for determining the polarization properties of light emitted, reflected or transmitted by a material using a laser scanning microscope with the tested material being illuminated point by point with a laser beam of known polarization state. According to the invention the light beam with a polarization state modified by the material or the light emitted by the material is being examined by measuring the intensity of two different polarization components of a selected light beam received from each point of said material essentially at the same time and assigning a signal obtained by processing the two intensity signals to a respective point of an image of said material. The apparatus has a polarization state generator between the laser light source and the material being tested, and a detector in a light beam for determining the intensity of light with a polarization state modified by the material or the intensity of light emitted by the material, the improvement of which is that a means for dividing the polarization components in space or time is used in front of the detector.

29 Claims, 6 Drawing Sheets

METHOD AND APPARATUS FOR DETERMINING THE POLARIZATION PROPERTIES OF LIGHT EMITTED, REFLECTED OR TRANSMITTED BY A MATERIAL USING A LASER SCANNING MICROSCOPE

CROSS-REFERENCE TO RELATED APPLICATIONS

This application is a continuation of the U.S. National Stage designation of co-pending International Patent Application PCT/HU01/00116, filed Nov. 16, 2001, the entire content of which is expressly incorporated herein by reference thereto.

FIELD OF THE INVENTION

The invention relates to a method and apparatus for determining the polarization properties of light emitted, reflected or transmitted by a material using a laser scanning microscope.

BACKGROUND OF THE INVENTION

Using a laser scanning microscope (LSM) selected points (well defined volume units) of the tested material are irradiated by a focused laser beam in response of which information on the intensity of the transmitted, reflected or emitted light is obtained which can be stored generally in digital form. The signal of the laser scanning microscope during scanning a field of predetermined width and length is used to obtain a picture of high resolution for detailed analysis. The picture quality may be further increased by using the LSM in confocal mode, thereby substantially excluding the disturbing effect of the light emanating from points other than the focus point. In most of the commercially available laser scanning microscopes (such as in Zeiss 410 or 510) the confocal mode is a basic feature but it may be used only for the reflected or emitted light (fluorescence). The confocal mode of the LSM provides for the non-destructive optical slicing of the sample and the reconstruction of three dimensional "images". Highly improved picture quality may be obtained by using a two or more photon laser excitation method which may be strictly limited to the tested area and thereby the disturbing effect of the background radiation (intensity) may be practically completely eliminated (A. Diaspro and M. Robello: Multi-Photon Excitation Microscopy to Study Biosystems, European Microscopy and Analysis, March 1999).

Laser scanning microscopes—when compared to the conventional microscopes and methods—provide a high quality and high resolution information of the sample structure. Nevertheless these methods do not provide any information on the anisotropy and many other physical interactions of the sample that may only be examined with polarization spectroscopy methods.

The use of polarized light provides images of the sample comprising information on the anisotropic structure, e.g. the spatial arrangement of the transition dipoles, and the physical interaction between each other and the microenvironment. The anisotropic properties of the materials influence generally the polarization properties of the light emitted, reflected or transmitted by the materials in an anisotropic way, therefore the examination of the polarization properties of the light emitted, reflected or transmitted by the materials enables conclusions relating to the optical anisotropy and also the molecular order of the tested material. Measurements carried out with polarized light (LD: linear dichroism, CD: circular dichroism) are described by T. C. Oakberg in Application note, Stokes Polarimetry, Hinds Instruments Inc., 1991 news. Similar method may be used for measuring the birefringence, too. The linear polarization of luminescence emission provides important information on the anisotropy of the emission dipoles, therefore the anisotropy value (r) characteristic for this provides an important information on the material structure not obtained by other techniques. The circular polarized luminescence (CPL) content of the emission (emitted light) provides important information on the chiral structure of the material when excited which may not be obtained in any other way. Further important information is the degree of polarization (P) of the fluorescence which allows conclusion on energy transfer between the dipoles, the microviscosity of the surrounding of the molecule, lifetime of an excitation and other important parameters. The definition, measurement and physical content of P, r and CPL is specified in detail by J. R. Lakovicz in his book "Principles of Fluorescence Spectroscopy" and I. Z. Steinberg in his report published in Methods in Enzymology.

During differential polarization imaging as described in detail by Kim et al. in a report published in Biophysical Journal two different images are produced of the sample using orthogonally polarized light, the intensity normalized difference of which provides information on the anisotropic structure of the material or sample. The CD, LD and other differential polarization values of transmitted light provide important information on the anisotropic structure of the material not available with other techniques.

The polarization properties of the fluorescence (emitted light) may be determined by placing a polarizer component (e.g. a polarizer filter) in front of the detector of the LSM, rotating the polarizer filter between two angular positions for trajection of the orthogonal components of linear polarized light and taking two pictures subsequently in both positions of the polarizer filter, in principle. Although this method may be carried out with the accessories of the Zeiss LSM 410, it does not provide satisfying results because of the variation of the intensity of fluorescence in time—especially in biological samples. A further problem may be the variation of the intensity of the illuminating laser light. Vibrations and movements of the sample or the stage may also lead to significant distortion.

U.S. Pat. No. 5,457,536 suggests an improvement to Zeiss LSM which makes the general purpose laser scanning microscope capable of point-by-point measuring the dichroism and the birefringence of the light transmitted through the sample. The laser beam directed to the sample is modulated with a polarization state generator interposed between the laser light source and the sample. For measuring the light transmitted through the sample there is a polarization analyzer on the other side of the object plane. The output of the analyzer is connected to a photodetector which is connected with an output to a demodulator unit. One drawback of this configuration is that in most of the LSM-s the confocal mode is not available during LD, CD and birefringence measurements which can only be carried out in transmission mode. This method does not enable the measurement of the polarization content of the emitted or reflected light, thus the measurement of the anisotropy in the linear or circular polarization (r, CPL) of the emission (emitted light). This is a major drawback in studying biological samples where the confocal fluorescence microscopy is widely used. In most of the biological applications important information on the spatial arrangement of the different components can be obtained by following the emission of several chromophores. Each item of this information carries different polarization information which can not be analyzed with said conventional techniques. In many LSM-s it is not possible or it is very difficult to modulate the laser light because of the optical fiber coupling of the laser light. It is also disadvantageous that there is no possibility to characterize in full detail the polarization content of the light and therefore some of the important parameters—assigned to the Mueller matrix elements—can not be determined.

Therefore one object of the invention is to provide a method and apparatus which combine the advantages of laser scanning microscopy and polarimetry with the combination resulting in more measured parameters with a single apparatus, or with different configurations of a single apparatus with special regard to the parameters of emitted fluorescence measured in confocal mode at a single or multiple wavelengths at substantially the same time, or with regard to the possibly most complete analysis of the polarization content of emitted, transmitted or reflected light.

A further object of the invention is to eliminate or compensate the errors resulting from wavelength dependency and the polarization distortion of the optical devices during the measurements.

SUMMARY OF THE INVENTION

These objectives are achieved by a method for determining the polarization properties of light emitted, reflected or transmitted by a material using a laser scanning microscope with the tested material being illuminated point by point with a laser beam of known polarization state. In the method according to the invention the light beam with a polarization state modified by the material or the light emitted by the material is being examined by measuring the intensity of two different polarization components of a selected light beam received from each point of said material essentially at the same time and assigning a signal obtained by processing the two intensity signals to a respective point of an image of said material.

According to an aspect of the invention the difference of the intensity signals of said two polarization components is generated during said signal processing and the difference is divided in accordance with the measurement carried out by the values 1, $I_1+I_2$, $I_1+2I_2$ or any other value assigned to an element of the Mueller matrix and determined by measurement or calculation.

According to another aspect of the invention the light beam is divided into two different beams according to the polarization state or a predetermined percentage of the intensity of the light and in each of the divided light beams the intensity of only one of the polarization components will be measured.

According to a further aspect of the invention the phase between the polarization components of light beam received from the material is varied periodically according to a function with a predetermined frequency and shape between two end positions and the polarization components are measured subsequently with the same analyzer.

The phase between the polarization components of light beam received from the material is varied between the two end positions preferably according to a sinus function.

Also the wavelength dependency of the polarization properties can be determined by the method according to the invention, wherein the step of varying the phase between the polarization components of light beam received from the material is followed by a further step of dividing the light beam according to selected wavelengths and carrying out measurements in each of the divided light beams at the same time. The errors of the measured values may be compensated if necessary.

According to another aspect of the invention the phase between the polarization components of the illuminating light beam is varied periodically according to a function (preferably a sinus function) with a predetermined frequency and shape between two end positions and the FDLC and FDCD values are determined by measuring the intensity of the light emitted by the material periodically with a predetermined frequency (2 f and f) and phase.

Measurements in a confocal mode include also the step of selecting the light component received from the focus point of the laser light on the sample and excluding the light components received from points other than the focus point. This enables the optical slicing of the sample.

According to a further aspect of the invention a laser light that allows spatial and/or temporal intensity concentration is used for illuminating the sample and for causing two or more photon excitation in the molecules of the sample virtually at the same time. This method automatically provides the advantage of confocal measuring. Using very short irradiation times of the individual pixels the sample may be scanned and measured for a longer period of time without being influenced adversely by the laser light.

The method according to the invention provides for an easy way of determining the Stokes parameters (I,Q,U,V) in at least one of the light beams of the microscope.

The invention provides also a method capable of determining the elements of the Mueller matrix in a transmitted or reflected laser beam of the microscope by changing the polarization state of the illuminating laser light in four steps (depolarized, linearly polarized at 0 (or 90 degree), linearly polarized at +45 (or −45 degree), and circularly polarized) while determining the Stokes parameters (I,Q,U,V) in each of the said four states.

The objectives of the invention are achieved by an apparatus for determining the polarization properties of light emitted, reflected or transmitted by a material using a laser scanning microscope with a polarization state generator between the laser light source and the material being tested, and a detector in a light beam for determining the intensity of light with a polarization state modified by the material or the intensity of light emitted by the material. According to the invention a means for dividing different polarization components in space or time is used in front of the detector.

The apparatus according to the invention may comprise an optical component in the light beam received from the material for dividing the polarization components in space according to their polarization state or according to a predetermined percentage of the intensity with a detector in the light beams divided according to the polarization state of the polarization components or with a detector and an analyzer in front of the detector for selectively transmitting one of the polarization components in the light beams divided according to a predetermined percentage of the intensity.

In a preferred embodiment of the invention a photoelastic modulator (PEM, Kerr cell, or the like) is comprised in the light beam received from the material for dividing the polarization components in time and a passive polarization analyzer is provided in front of the detector.

For determining the wavelength dependency of the polarization parameters the apparatus according to the invention may comprise at least one wavelength selective beam splitter between the passive polarization analyzer and detector and further detectors may be provided in the light beams divided by the wavelength selective beam splitter.

For determining the Stokes parameters the apparatus according to the invention may include a second photoelastic modulator (PEM) between the photoelastic modulator and the passive polarization analyzer with the second photoelastic modulator (PEM) having an optical axis rotated by 45° relative to the optical axis of the first photoelastic modulator (PEM).

For determining the elements of the Mueller matrix the apparatus according to the invention may be provided with a polarization state generator comprising depolarizer, a linear or circular polarizer and an optical phase retarder or any combination thereof.

For measuring the FDLD (fluorescence detected linear dichroism) value and the FDCD (fluorescence detected circular dichroism) value the apparatus according to the invention may be provided with a polarization state generator comprising a passive polarization optical component and a photoelastic modulator (PEM).

For improving the signal to noise ratio the apparatus according to the invention may be provided with a polarization state generator comprising a photoelastic modulator (PEM) positioned between two passive linear polarizer with a polarization plane parallel or perpendicular to each other and the optical axis of the photoelastic modulator (PEM) set at 45° relative to the passive linear polarizers and further comprising a depolarizer behind the second linear polarizer.

For converting and processing the measured signals and compensating the errors during measuring the apparatus according to the invention may be provided with a signal processing unit which is connected to the output of the detector(s). The signal processing unit comprises at least one lock-in amplifier, a low-pass filter and an analog-digital converter. In case of digital signal processing and an imaging unit with an analog input also a digital-analog converter is required in the signal processing unit.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF PREFERRED EMBODIMENTS

Figure 1:
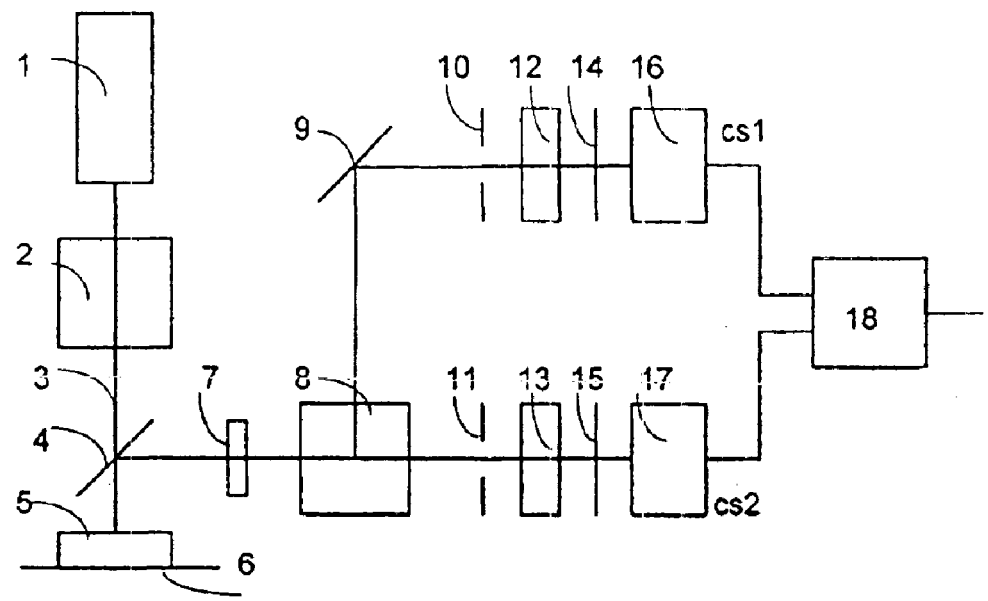
FIG. 1 is a schematic diagram of an apparatus according to the invention with two channels for working in emission or reflection mode.

FIG. 1 depicts a two channel configuration with a sample 5 on object table 6 which is illuminated with a laser light of laser light source 1 with the laser light routed through polarization state setting unit 2. The reflected light or the fluorescence are deflected by beam splitter 4 (for example semitransparent mirror). This way two light beams are generated by a second beam splitter 8. In both light beams there is a detector 16 and 17 producing an output signal proportional with the intensity of light which is input to signal processing units 18. In each of the channels cs1 and cs2 the intensity of only one polarization component is measured. A semitransparent mirror can be used as a beam splitter 8. In this case the entering light beam will be separated in a given proportion of the intensity. In one of the divided light beams a further mirror 9 may be placed for deflecting a selected light beam. Both of the divided (deflected) light beams contain all polarization components, therefore the polarization components to be measured must be selected by a passive polarization analyzer 12 and 13 located in front of the detectors 16 and 17. As a beam splitter 8 also a polarization beam splitter (e.g. a Wollaston prism, or the like) can be used for transmitting only a first polarization component in the first divided beam and transmitting only a second polarization component in the second divided beam. Polarization beam splitters are commercially available from Melles Griot or Oriel. Special polarization beam splitters are also available from OZ Optics, Ltd. A further mirror 9 may be placed in the deflected light beam if necessary for deflecting in this case the light beam of channel cs1 to detector 16. When using a polarization beam splitter 8 passive polarization analyzers 12 and 13 are not needed. In the light beams of the channels cs1 and cs2 and in front of the detectors 16 and 17 also colour filters 14 and 15 may be used for rejecting the intensity of the undesired light. Diaphragms 10 and 11 positioned in the light beam of channels cs1 and cs2 may be necessary for confocal imaging. Measurements in a confocal mode include also the step of selecting the light component received from the focus point of the laser light on the sample and excluding the light components received from points other than the focus point. This enables the optical slicing of the sample. In the light beam received from the sample 5 preferably before the beam splitting a phase retarder 7 (quarter wavelength plate) may also be used for enabling the selection of the circular polarized components even if only linear polarization beam splitters or analyzers are used. The arrangement of FIG. 1 is one possible embodiment for measuring the intensity of two different polarization components at the same time received from the sample illuminated pixel by pixel by the laser scanning microscope. The analog signals proportional to the intensity values are input to the signal processing unit 18 where the necessary conversions, calculations and corrections will be carried out. On the basis of the two polarization components $I_1$ and $I_2$ which are substantially orthogonal to each other the output signal will be calculated with the one of the following formula or one of the formula used to determine the elements of the Mueller matrix.

$$I_{out} = I_1 - I_2 \quad (1)$$

$$I_{out} = (I_1 - I_2)/(I_1 + I_2) \quad (2)$$

$$I_{out} = (I_1 - I_2)/(I_1 + 2I_2)$$

Formula (3) is preferably used in case of measuring anisotropy of emission dipoles oriented in a cylindrical symmetry. The polarization components measured with the method according to the invention are orthogonal to each other. The resulting values of the above formulas are determined by the signal processing unit 18. One of the above calculations is carried out for each of the pixels (illuminated points of the sample) and the result is stored in a storage means. The stored image information is displayed on a display means (screen, monitor, etc.) by a video signal processing unit and software.

Figure 7:
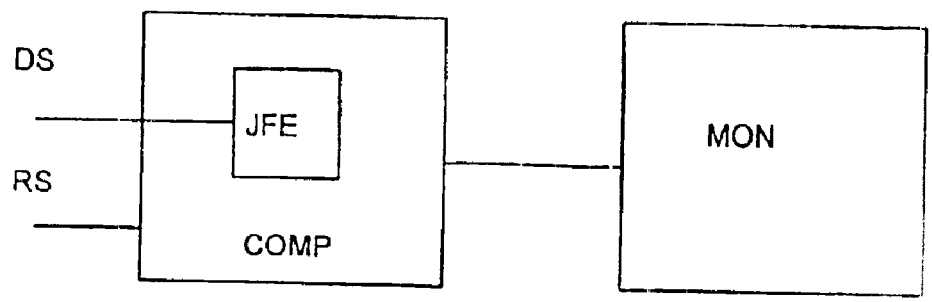
FIG. 7 is a schematic diagram of a signal processing and imaging unit for displaying the measured values.

In one embodiment the output signal of the signal processing unit 18 is simply lead to the image signal input of the LSM. In another embodiment as depicted in FIG. 7 the synchron signal for scanning/rastering the laser light of the LSM and the output signal of the signal processing unit 18 is further processed by an electronic control unit, e.g. a computer COMP to an image signal and the image is then displayed on a monitor MON.

Figure 2:
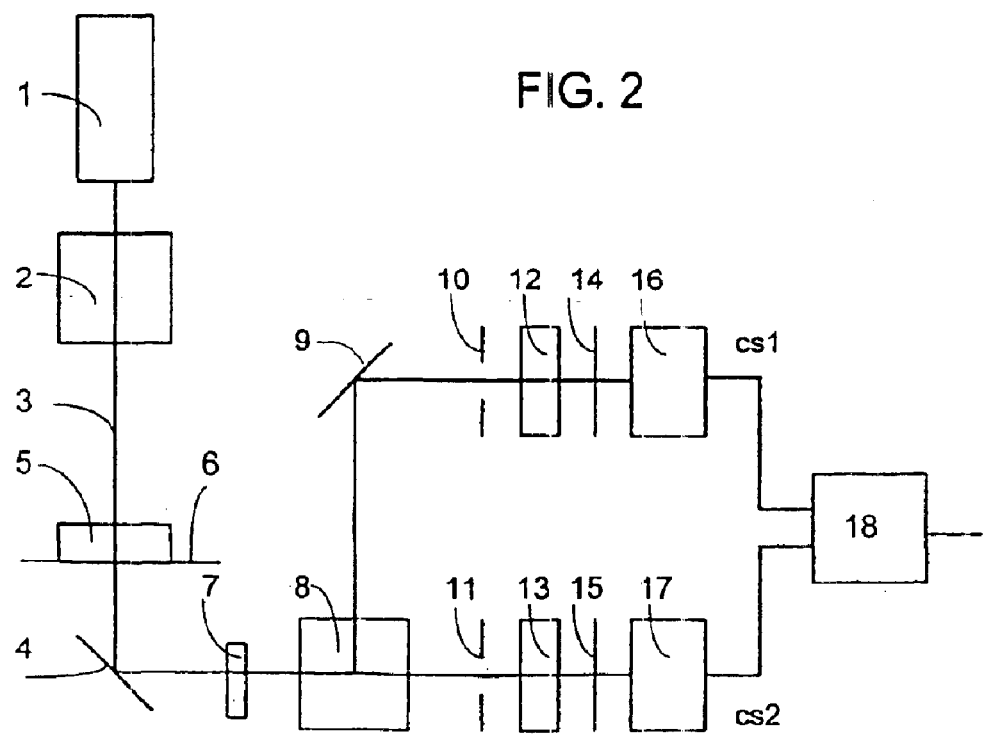
FIG. 2 is a schematic diagram of the apparatus according to the invention with two channels for working in transmission mode.

The embodiment shown in FIG. 2 differs from the embodiment seen in FIG. 1 only in the laser light 3 passing through the sample 5 and the measurements are carried out on the transmitted light. For the measurements the same elements are used as seen in FIG. 1. The same elements of FIG. 2 are marked with the same reference signs of the same elements of FIG. 1. The mirror 4' in this example is not necessarily a semitransparent mirror, any optical mirror can be used.

Figure 3:
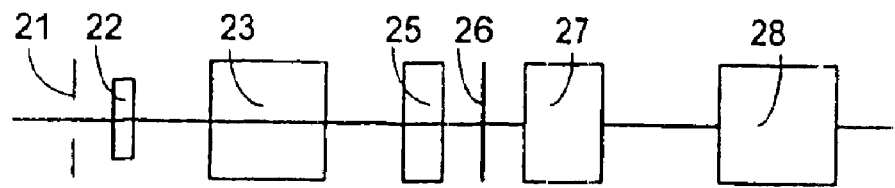
FIG. 3 is a schematic diagram of the apparatus according to the invention with one channel and working according to the modulation principle.

In FIG. 3 another embodiment according to the invention is shown for the measurement of the different polarization without splitting the light beam received from the sample, that is using only one light beam. To accomplish this, we use an arrangement to separate the polarization components in time. For this purpose the phase between the polarization components of light beam received from the sample 5 is varied periodically according to a function with a predetermined frequency and shape (preferably according to a sinus function) between two end positions and the polarization components are measured subsequently through the same analyzer 25 with the same detector 27. For periodically varying the phase between the polarization components a polarization modulator, such as a photoelastic modulator (PEM), an electro-optical modulator (EOM), an opto-acoustic modulator, a Kerr cell, a Pockels cell or the like. In a preferred embodiment as shown in FIG. 3 a photoelastic modulator 23 is used in front of a detector 27 for sensing the light intensity and providing an output signal proportional thereto. For selecting only one polarization component a passive polarization analyzer 25 is used between the detector 27 and the photoelastic modulator 23. A suitable photoelastic modulator is available from Hinds Instruments under the trade name I/FS50, but other types or means with the same effect may be used. The output of detector 27 is connected with an input of signal processing unit 28 in the same way as already seen in FIGS. 1 and 2.

In front of the detector 27 also a colour filter 26 may be used for rejecting the intensity of the undesired background light. Diaphragm 21 positioned in the light beam may be necessary for confocal imaging. In the light beam received from the sample 5 preferably before the photoelastic modulator 23 a phase retarder 22 (quarter wavelength plate) may also be used for enabling the selection of the circularly polarized components even if only a linear polarization analyzer is used.

In the said one-channel configuration the number of elements used for the measurements can be reduced substantially by one half resulting also in substantial reduction of the costs. Beside the economical advantage it is a further technical benefit that the measurement can be carried out in the same light beam with the same optical and electro-optical devices which reduces the errors due to tolerances of the devices. The photoelastic modulator 23 is controlled by an electric signal with a predetermined frequency and shape, such as sinusoidal alternating voltage, with the control resulting in a sinusoidal alternating width d of the photoelastic modulator according to $d = d0 + A*\sin(2\pi f t)$. The initial width of the photoelastic modulator without any control voltage is d0. The maximal width is d0+A and the minimal width is d0−A. In its ground state the photoelastic modulator does not change the polarization properties of the transmitted light. If the maximal change of the width of the photoelastic modulator is lambda/4 (lambda is the wavelength of the light used) the linearly polarized incident light will be converted by the photoelastic modulator in its d0+A state into a circularly left or right polarized light and in the d0−A state of the photoelastic modulator the output light is converted into a circularly right or left polarized light. If the maximal change of the width of the photoelastic modulator is lambda/2 (lambda is the wavelength of the light used) the linearly polarized incident light will be converted by the photoelastic modulator in its d0+A and d0−A state into a linearly polarized light with a polarization plane rotated at 90 degrees with respect to the polarization plane of the incident light. It should be noted that in this case when reaching the lambda/4 positions circularly left of right polarized light is provided depending on the direction of change.

Thus it can be stated that using a control resulting in maximal changes in the width A=lambda/2 at the output of the controlled photoelastic modulator 23 a linearly polarized light with the same direction will repeatedly appear with a frequency 2 f with regard to the frequency f of the control voltage and using a control resulting in maximal changes in the width A=lambda/4 a circularly polarized light with the same direction will repeatedly appear with the frequency f of the control voltage.

Figure 10A:
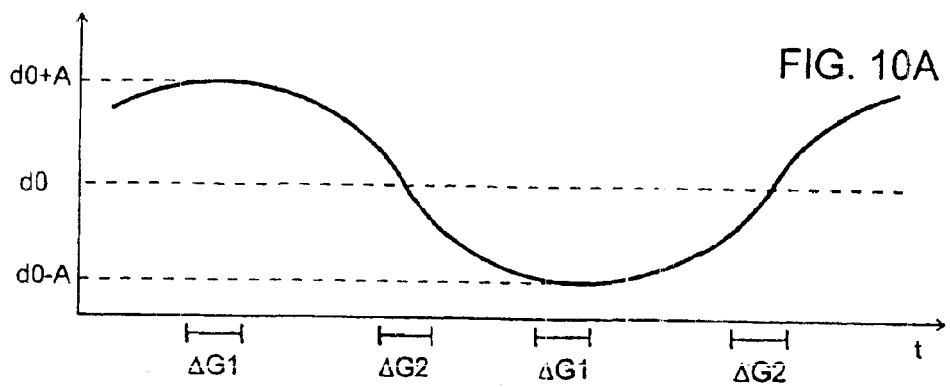
FIG. 10 is diagram illustrating the method for compensating the sinusoidal error of the photoelastic modulators.
Figure 10B:
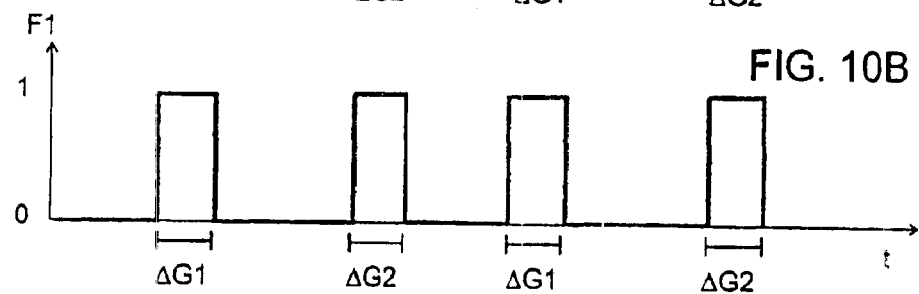
Figure 10C:
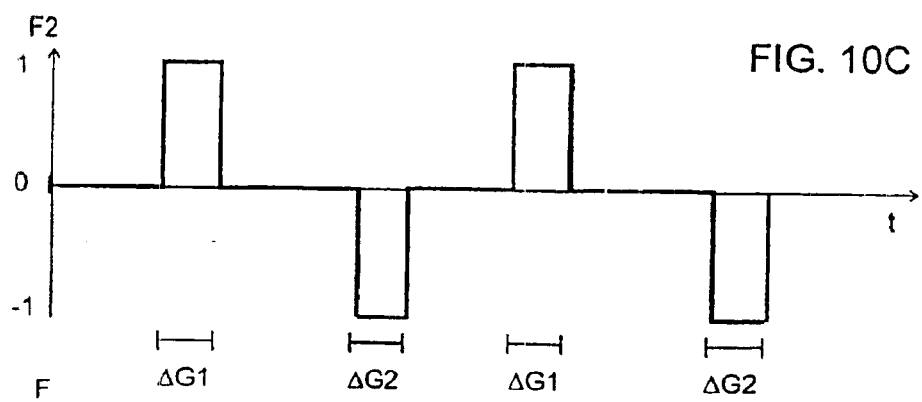
Figure 10D:
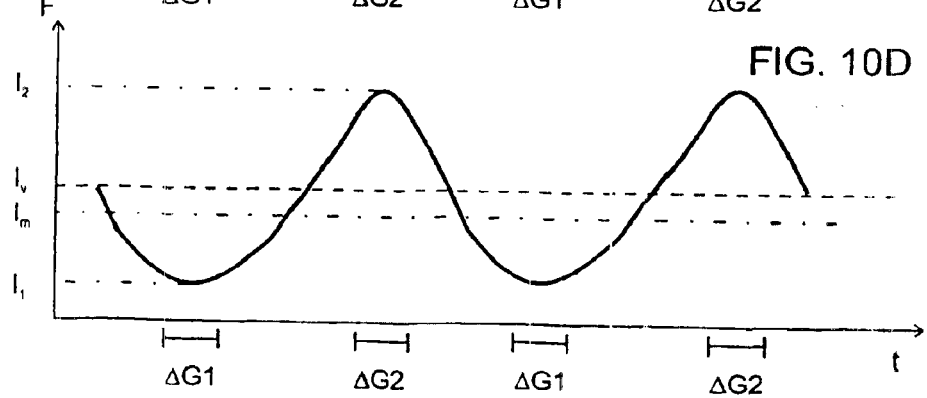

The linear polarization analyzer in front of the detector transmits only substantially one selected linear polarized light having a polarization plane parallel to the polarization axis of the analyzer, which in return results in a maximum of the detector signal and all other polarized light components result in a smaller value of the detector signal. The linear polarized light with a polarization direction orthogonal to the polarization axis of the analyzer will provide a minimum of the detector signal. If the photoelastic modulator 23 is positioned in front of the analyzer 25 for providing in the end positions linearly polarized light having a polarization angle of 0 and 90 degrees relative to the polarization axis of the passive polarization analyzer 25 the output signal of the intensity will periodically change with a frequency 2 f relative to the frequency f of the control voltage as shown in FIG. 10D. The signal processing is different from the signal processing explained in connection with FIG. 1. While the arrangement of FIG. 1 provided static signals for further processing, the configuration of FIG. 3 provides polarization components and their measured intensity values change in time periodically with a relatively high frequency of at least 10 kHz, preferably at least 100 kHz. Under such circumstances the measurement has to be carried out synchronized to the sinusoidal control voltage of the PEM, exactly in predetermined phase positions. Repeated measurements at a predetermined frequency in predetermined phase positions can be carried out with a phase sensitive or "lock-in"amplifier which is capable of carrying out measurements at a predetermined frequency f or in dual mode at predetermined frequencies f and 2 f. The phase sensitive (lock-in) amplifiers provide in a conventional difference mode a difference intensity value $\Delta I = I2 - I1$. Phase sensitive (lock-in) amplifiers working at relatively high frequencies of at least 10 kHz, preferably at least 100 kHz are available from several manufacturers, such as EG&G or Jupiter.

Figure 8A:
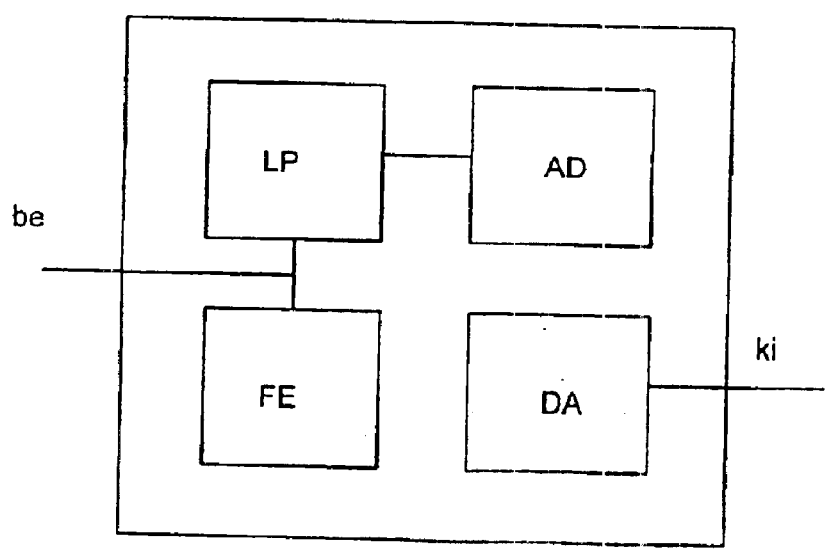
FIG. 8 is a schematic diagram of the signal processing unit used in the apparatus according to the invention.

The signal processing unit 28 to be used with a configuration of FIG. 3 may be configured as shown in FIG. 8A comprising a low pass filter LP and a phase sensitive amplifier FE connected to the output of the detector and comprising an analog-digital converter AD connected to the output of the low pass filter LP. In case of digital signal processing and an imaging unit having an analog input also a digital-analog converter DA is required. The present LSM-s manufactured by Zeiss have an imaging unit with an analog input, therefore the digital-analog converter DA provides for preserving the compatibility.

Most of the LSM systems (also the LSM of Zeiss type 410) are suitable for measuring the intensity of the fluorescence emitted by the sample having components of different wavelength by separating each emission wavelength and measuring with a special detector (typically with a photoelectron multiplyer). The excitation may occur at a single frequency or at more frequencies. For the separation dichroic mirrors may be used. In the configuration for measuring at different wavelengths shown in FIG. 4 the illumination of the sample 5 is the same as seen in and described in connection with FIG. 1. In the light beam received from the sample 5 and deflected by the semitransparent mirror 4 there is a photoelastic modulator 31 (such as FS50 available from Hinds) and a passive polarization analyzer 32. The analyzer is followed by dichroic mirrors or by dichroic beam splitters 33 for separating the light received from the sample according to the different wavelengths and an optical mirror 34 if necessary for deflecting a separated light beam. With the photoelastic modulator 31 (such as of Hinds type FS5O) positioned in front of the dichroic mirrors or beam splitters 33 all wavelength components of the fluorescence may be modulated at the same time. Although the modulation depth of the polarization state will be different due to the different wavelengths, it can be calculated and with a correction factor compensated. In this manner the method as described in connection with FIG. 3 can be extended to more wavelengths. With regard to the fact that most of the dichroic beam splitters are polarization state selective, the passive polarizer 32 may in some cases be omitted or replaced by dichroic mirrors. Commercially available are also dichroic beam splitters that are in a large wavelength range insensitive to the polarization state of light. In the different wavelength selective channels the intensity is detected at the same time in detectors 37 and the detected signals are directed to a common signal processing unit 38 for performing a signal processing described above in detail. This configuration requires the application of multiple means or multichannel means for measuring. The signal processing is simplified by the fact that in this configuration the modulating frequency is the same in all channels.

A diaphragm 35 positioned in the light beam may be necessary for confocal imaging and a colour filter 36 may be used for rejecting the intensity of the undesired background light The signal processing unit 38 used with the configuration shown in FIG. 4 may be the same as shown in FIG. 8A and described in detail in connection with FIG. 3. For processing the threefold amount of data of the three channels the signal processing unit of FIG. 8A may be tripled, or in case of sufficiently high processing speed it is also possible to connect alternately (multiplexing) the outputs of the detectors 37 of the three channels to the input of the signal processing unit 38.

Figure 4:
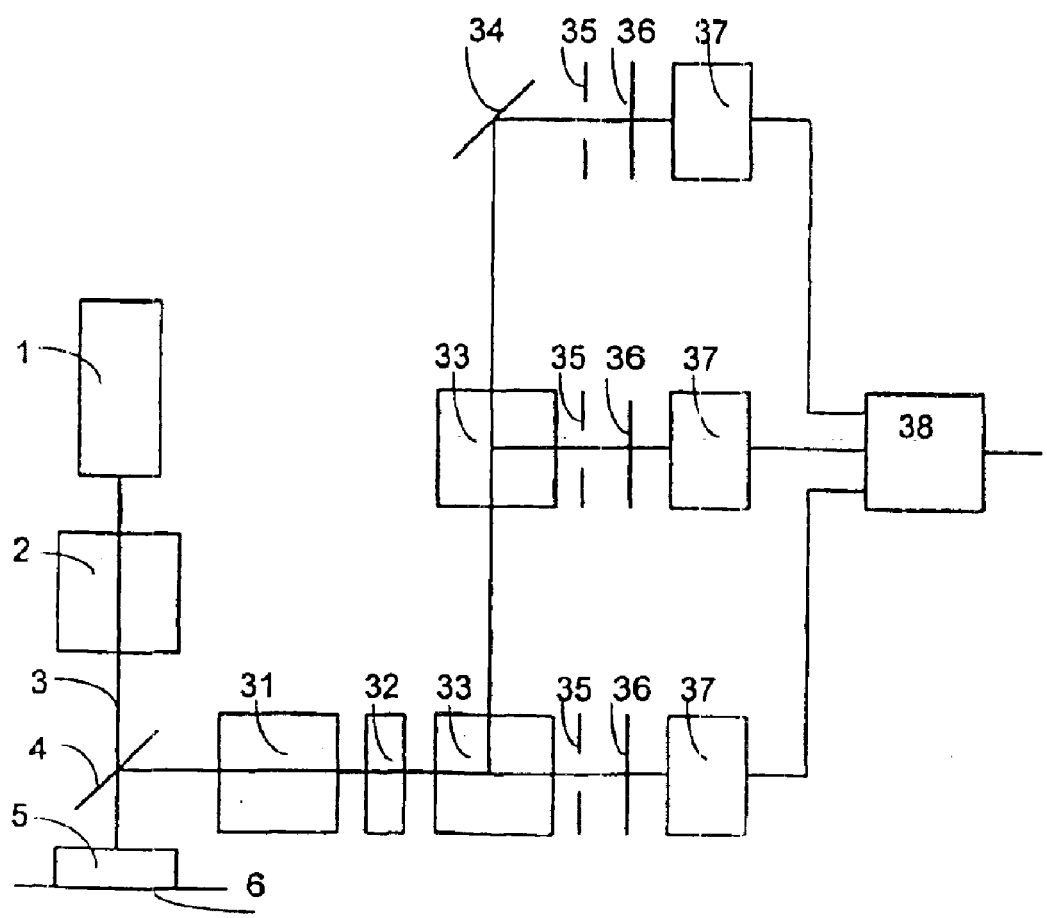
FIG. 4 is a schematic diagram of the apparatus according to the invention working according to the modulation principle for measuring at different wavelengths.

The arrangement of FIG. 4 may—in case of a single emission band—also be used for separating the different polarization components of the light beam. For this purpose instead of the single modulator and analyzer before the deflection an individual modulator and analyzer has to be applied in each channel. The configuration of one channel is shown in FIG. 3. According to this, in two channels the difference of the intensity $I(90°)-I(0°)$ and $I(+45°)-I(-45°)$ of the linear polarized emission and the circularly polarized component can be measured. The measurement of $I(+45°)-I(-45°)$ is performed in the same way as the measurement of $I(90°)-I(0°)$ but the modulator is set to 0° and the analyzer to 45°. This may be especially important in measurements of anisotropy. During these measurements also a value proportional to the full intensity of the fluorescence may be determined and thus the differences in sensitivity may be compensated. This will be described in more detail in connection with FIG. 10. Using three channels all characteristic parameters, e.g. all components of the Stokes vector (I,Q,U,V) of the polarization state of the emitted fluorescence or reflectance may be determined and displayed as an image as described above.

Figure 5:
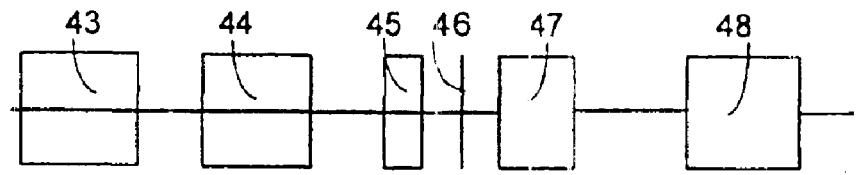
FIG. 5 is a schematic diagram of the apparatus according to the invention for measuring the Stokes parameters.
Figure 6A:
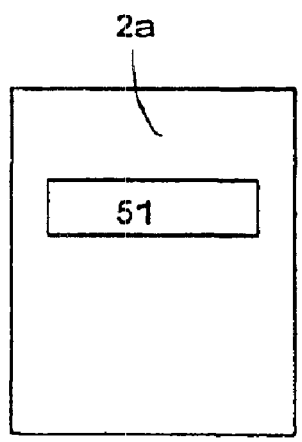
FIG. 6 is a schematic diagram of the apparatus according to the invention for determining the elements of the Mueller matrix.
Figure 6B:
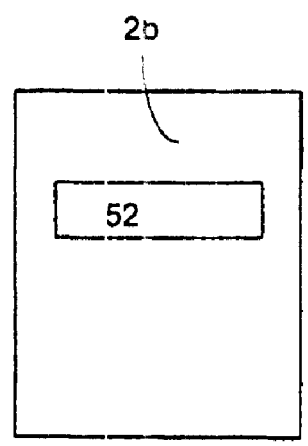
Figure 6C:
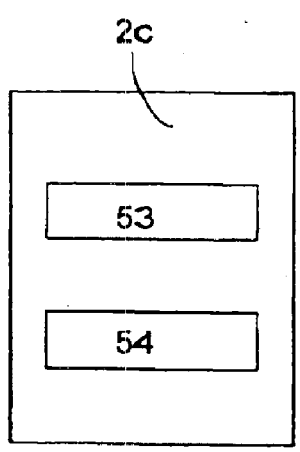
Figure 6D:
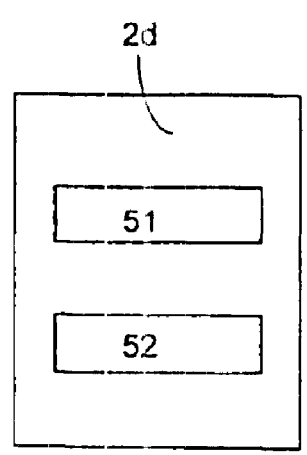
Figure 8B:
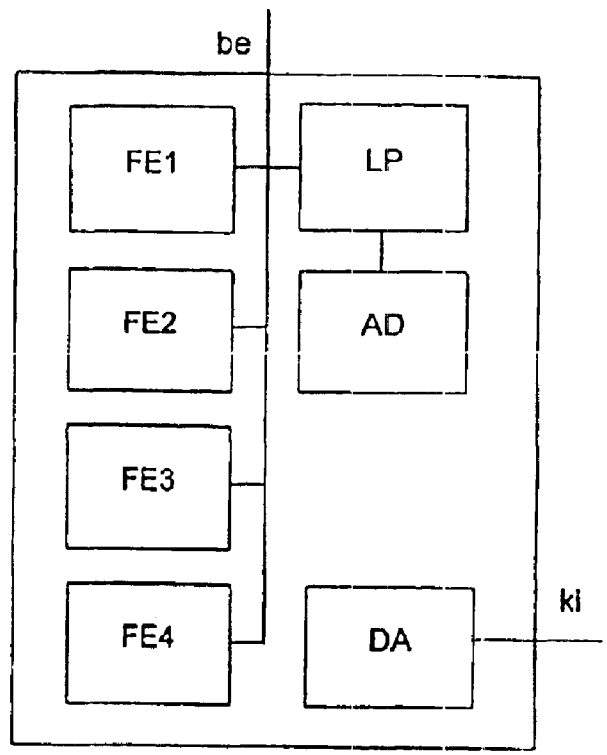

It is known to use a one channel method to determine the values of the Stokes vector or the state of the polarized light. By implementing this method in a laser scanning microscope (LSM) all values (I,Q,U,V) of the Stokes vector may be measured and displayed as an image (FIG. 5). For this purpose two photoelastic modulators 43 and 44 are positioned in series in the light beam received from the tested sample. The optical axis of the first photoelastic modulator 43 has an angle of 45 degrees and the second photoelastic modulator has an angle of 0 degree relative to a reference plane. Between the second photoelastic modulator 44 and the detector 47 a passive polarization analyzer 45 (such as a Glann-Thompson prism) is used with an optical axis having an angle of 22.5 degrees with the same reference plane. The output of the detector 47 is connected to signal processing unit 48 similar to the embodiments described before. In this case the signal processing unit 48 comprises three phase sensitive (lock-in) amplifiers FE1 . . . FE3 and one low pass filter LP as shown in FIG. 8B. For determining the intensity $I_m$ without error compensation a digital low pass filter is used. For compensating the error during measuring the intensity a fourth phase sensitive (lock-in) amplifier FE4 is needed. In case of digital signal processing an analog-digital converter AD is connected to the analog output of the low pass filter LP. In order to maintain compatibility with the imaging unit of the LSM having an analog input also a digital-analog converter DA is required. As a phase sensitive (lock-in) amplifier a DPSD (digital phase sensitive detector) manufactured by KFKI (Budapest) may be used which contains in dual configuration two phase sensitive amplifiers.

The implementation of the above imaging methods is significantly supported if the different functions of the signal processing unit (SPU) (phase sensitive amplifying, frequency selection, signal conditioning) are controllable. This is accomplished on a single DPSD board (KFKI, Budapest)

which is a low level programmable device providing the following functions. The input signal may be multiplied by any periodical scalar signal before calculating an average, which means that it can not only measure the amplitude of a signal of a selected frequency in difference mode—like the conventional phase sensitive (lock-in) amplifiers—but it is also capable of measuring the same in addition mode. In difference mode the output signal is responsive to the magnitude of the input signal at a phase Φ minus the magnitude of the input signal at a phase Φ+π. In the addition mode the output signal is responsive to the magnitude of the input signal at a phase Φ plus the magnitude of the input signal at a phase Φ+π. The scalar product of two functions is in general P=∫f1(t)*f2(t). The multiplier function for the addition mode is shown in FIG. 10B and the multiplier function for the difference mode is shown in FIG. 10C.

The values of the Stokes vector are determined as described below.

I, intensity: the $I_m$ signal of the low pass filter LP compensated with the signal $(I_1+I_2+2I_m)$ of phase sensitive (lock-in) amplifier FE4 which works in addition mode of PEM 43 or 44 at a frequency 2 f.

Q, 0°–90° linearly polarized component: signal of FE working in difference mode at a frequency 2 f of PEM 44.

U, ±45° linearly polarized component: signal of FE2 working in difference mode at a frequency 2 f of PEM 43.

V, circularly polarized component: signal of FE3 working in difference mode at a frequency f of PEM 43 or 44.

The values measured may be—after conditioning—directed to a suitable input of the imaging unit (video signal processing board) of the LSM for displaying the differential polarization (DP) values as a picture similar to the intensity picture in "conventional" mode.

According to another aspect of the invention, also the synchron signals for scanning the pixels in x and y direction may be used directly by a suitable image processing circuit (FIG. 7). As a consequence, it is possible to carry out the image processing independently from the image processing of the LSM while maintaining the compatibility of storing displaying the images with the LSM images. The advantage of this method when compared to the measurement according to FIG. 4 is that only one detecting channel is needed for the measurement and after relocating the detector it may be used as an external unit. The polarization image may be obtained without the further use of the LSM and that is independently of its hardware and software properties.

FIG. 6 shows different types of the polarization state setting unit which in combination with the arrangement of FIG. 5 provide a possibility for determining all of the Mueller matrix elements in transmission mode by using different known polarization states of the illuminating light. For this purpose the configuration of FIG. 5 is positioned behind the sample (behind mirror 4 in FIG. 2). The elements of the Mueller matrix will be determined according to the invention with a method comprising the step of changing the polarization state of the illuminating laser light in four steps (depolarized, linearly polarized at 0 (or 90 degree), linearly polarized at +45 (or −45 degree), and circularly polarized) while determining the Stokes parameters (I,Q,U,V) in each of the said four states. For this purpose a polarization state setting unit 2a–2d comprising depolarizer 51, a linear or circular polarizer 52,53 and an optical phase retarder 54 or any combination thereof is used. In FIG. 6A . . . 6D four different polarization state setting units 2a . . . 2d are shown which produces different but in the time constant polarization state laser light. The polarization state setting unit 2a comprises a depolarizer 51 for depolarizing the laser light which might be polarized and which illuminates the tested sample with a depolarized laser light. The polarization state setting unit 2b comprises a polarizer 52 which may be a linear or a circular polarizer as required. The polarization state setting unit 2b illuminates the tested sample with a linearly or circularly polarized laser light and may be used when the laser light was originally depolarized. The polarization state setting unit 2c comprises a linear polarizer 53 and a phase retarder 54 behind the linear polarizer 53 for illuminating the tested sample with a circularly polarized laser light and may be used when the laser light was originally depolarized. The polarization state setting unit 2d comprises a depolarizer 51 and a polarizer 52 behind the depolarizer 51. The polarizer 52 may be a linear or a circular polarizer as required. The polarization state setting unit 2d illuminates the tested sample with a linearly or circularly polarized laser light and may be used when the laser light was originally polarized.

Figure 9:
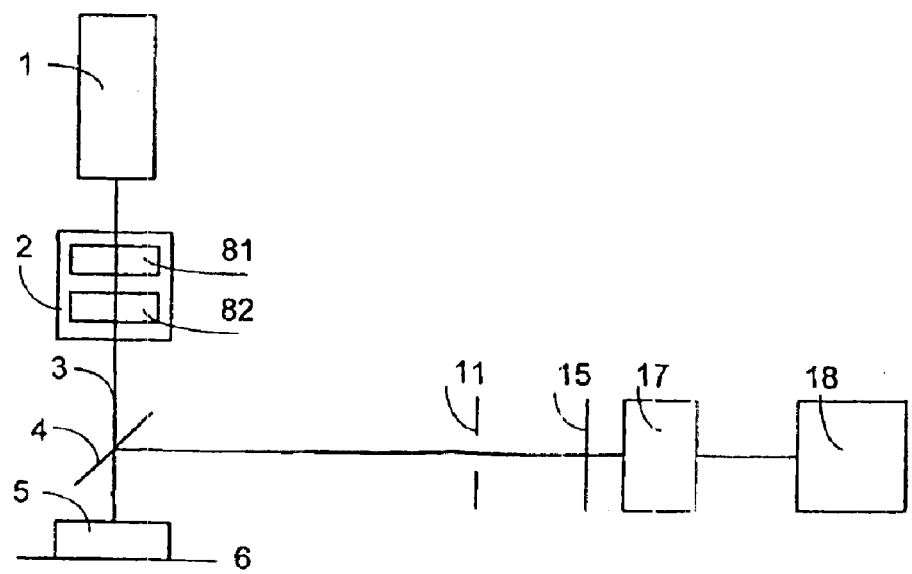
FIG. 9 is a schematic diagram of the apparatus according to the invention for determining the FDLD and FDCD values.

FIG. 9 depicts a further configuration according to the invention for measuring the fluorescence detected linear dichroism (FDLD) and the fluorescence detected circular dichroism (FDCD). For this purpose the polarization state setting unit 2 comprises a linear polarizer 81 and a photoelastic modulator 82 behind it. If the laser light source 1 provides a linearly polarized laser light the linear polarizer 81 may be omitted. With this arrangement the exciting laser light may be modulated to obtain different polarization states. The path of the luminescent light has not to be changed in the LSM. This provides an arrangement more simple than that seen in FIG. 1. The same elements with the same function have been marked with the same reference sign as used in FIG. 1. The signal processing is performed with a demodulation method similar to the method described above. The value of FDLD is measured at a frequency 2 f and the value of FDCD is measured at a frequency f and the image processing is also the same as described above in detail.

According to the invention a high power laser light allowing spatial and/or temporal intensity concentration may also be used for illuminating the sample and for causing two or more photon excitation in the molecules of the sample virtually at the same time. Using the known fact that two-photon-excitation falls off with the square of the distance from the focus a dramatic reduction of background fluorescence is obtained and thus the attainable spatial resolution is substantially improved, while the adverse effects of laser light can be minimized.

The exact value of the intensity I=I1+I2 can not be determined with the conventional methods using a low pass filter. The reason of the error and a correction method according to the invention will be described in more detail in connection with FIG. 10. FIG. 10A shows the variation in width d of the photoelastic modulator (PEM) due to a sinusoidal alternating control voltage as a function of time. As it can be seen in FIG. 10A the widths of the PEM under control of a sinusoidal alternating voltage varies also sinusoidal according to $d=d0+A*\sin(2\pi ft)$. In a ground state without any excitation of the PEM the polarization state of light passing through the photoelastic modulator does not change. In case of A=lambda/2 the PEM rotates by 90 degrees the polarization plane of incident light in the states of maximal or minimal width d0+A or d0−A. FIG. 10D shows the intensity value measured by a detector behind a linear polarization analyzer as a function of time wherein the control of the PEM is identical with the control seen in FIG.

10A. The analyzer is set to have an optical axis parallel to the polarization plane of a linearly polarized light passing through an unexcited PEM. This arrangement provides a maximal intensity $I_2$ in each position do. In the positions d0+A and d0−A the polarization plane of the linearly polarized light is orthogonal to the optical axis of the analyzer, therefore the intensity $I_1$ measured with the detector is minimal. For the intensity function is not sinusoidal the DC component separated by the digital low pass filter does not provide the intensity $Iv=(I_1+I_2)/2$ but $I_m$. Using the fourth phase sensitive amplifier FE4 in addition mode $S_+=I_1+I_2-2I_m$ may be obtained. As $I_m$ has already been determined the compensated value of the intensity may be calculated according to $$I=I_1+I_2=S_++2I_m$$

This method for compensating the error of the intensity measured has the advantage when compared to prior publications, for macroscopic dichroism measurements, that it does not require any limitation of the modulation depth and therefore it provides a more accurate compensation.

The systematic errors of the DP measurements due to the different optical elements affecting the polarization state may be compensated by correction methods, which may be performed during digital signal processing.

With the intensity modulation of the exciting (illuminating) light the photoselection may be eliminated and the signal to noise ratio may be improved.

The laser light used in LSM is typically polarized. As the absorption and the emission is dependent on the polarization state of the illuminating light, the image obtained from a sample may vary depending on the polarization state of the light used. In the LSM images it produces undesired overexposures or underexposures or even diminishing of details. It is in anisotropic samples extremely significant. This effect may be eliminated by using a depolarizer in the polarization state setting unit as proposed in FIG. 6A. This may be used in cases of transmission, fluorescence or reflectance as well. A passive depolarizer positioned in the exciting/illuminating light beam may however cause inhomogenities at microscopic level and the output is in many cases not satisfactory either.

Similar to the method used in FDLD/FDCD measurements a PEM may be used for varying the polarization state of the irradiating light in time instead of a de-polarizer. After a suitable gating or averaging of the detector signal the photoselection may be eliminated without any disturbing side effect as the illuminating (exciting) light comprises all polarization directions during the time the laser light is focused on one point and the averaging takes place.

The method of modulating and demodulating may also be used for improving the signal to noise ratio if no polarization measurements are carried out. For this purpose the polarization state generator comprises a photoelastic modulator (PEM) positioned between two passive linear polarizers with a polarization plane parallel or perpendicular to each other and the optical axis of the photoelastic modulator (PEM) set at 45° relative to the passive linear polarizers. Also a depolarizer behind the second linear polarizer may be used if necessary. This arrangement provides a sinusoidal alternating intensity with a frequency 2 f relative to the frequency f of the PEM. The demodulation may be carried out with a single phase sensitive (lock-in) amplifier at the frequency 2 f. If the laser light source provides a distortion free linearly polarized laser light the linear polarizer on the side of the laser light source may be omitted. If the photoselection does not affect the measurements adversely or the compensation is performed in a dynamic mode as described above, also the depolarizer may be omitted. This method for improving the signal to noise ratio has the advantage when compared to other methods using high intensity modulating frequencies that the FDLD and FDCD measurements and the photoselection compensation may be performed with the same components.

What is claimed is:

1. A method for determining differential polarization quantities of a test material using a laser scanning microscope comprising:

illuminating a test material point by point with a single laser beam of known and adjustable polarization state;

receiving light from each illuminated point of the material, the light having a polarization state modified by the material or a polarization state of the light being emitted by the material;

measuring an intensity of two different polarization components of the light received from each illuminated point of the material substantially at the same time and assigning a signal to each measured intensity; and processing the two measured intensity signals and assigning a signal, a differential polarization quantity, to a respective point of an image of the material.

2. The method of claim 1, wherein a difference of the intensity signals of said two polarization components is generated during said signal processing, and the difference is divided in accordance with the measurement carried out by the values 1, $I_1=I_2$, $I_1=2I_2$ or any other value assigned to an element of the Mueller matrix and determined by measurement or calculation.

3. The method of claim 1, further comprising dividing the light into two different light beams according to one of (1) the polarization state and (2) a predetermined percentage of the intensity of the light, wherein the intensity of only one of the polarization components is measured in each of the divided light beams.

4. The method of claim 1, further comprising:

periodically modifying the polarization state of light received from the material by varying a phase between the polarization components according to a function with a predetermined frequency and shape between two end positions, wherein the polarization components are measured subsequently with the same analyzer.

5. The method of claim 4, wherein the phase between the polarization components of light received from the material is varied between the two end positions according to a sinusoidal function.

6. The method of claim 4, wherein after the phase is varied between the polarization components of light received from the material, the light is divided Into light beams according to selected wavelengths, each of the divided light beams is measured at the same time, and errors in the measurements are compensated.

7. A method for determining polarization properties of light emitted, reflected or transmitted by a material using a laser scanning microscope comprising:

illuminating a test material point by point with a laser beam of known polarization state;

receiving light from each illuminated point of the material, the light having a polarization state modified by the material or the light being emitted by the material;

measuring an intensity of two different polarization components of the light received from each illuminated point of the material substantially at the same time and assigning a signal to each measured intensity; and processing the two measured intensity signals and assigning a signal to a respective point of an image of the material;

wherein a phase between the polarization components of the light from the illuminated points is varied periodically according to a function with a predetermined frequency and shape between two end positions, and a fluorescenee detected linear dichroism value and the fluorescence detected circular dichroism value are determined by measuring the intensity of light emitted by the material periodically with a predetermined frequency (2f and f) and the phase.

8. The method of claim 7, wherein the phase between the polarization components of the illuminating laser beam is varied between the two end positions according to a sinusoidal function.

9. The method of claim 1, further comprising:
selecting a light component received from a focus point of the light from the laser beam on the sample and excluding light component received from points other than the focus point.

10. A method for determining the polarization properties of light emitted, reflected or transmitted by a material using a laser scanning microscope comprising:
illuminating a test material point by point with a laser beam of known polarization state;
receiving light from each illuminated point of the material, the light having a polarization state modified by the material or the light being emitted by the material;
measuring an intensity of two different polarization components of the light received from each illuminated point of the material Substantially at the Same time and assigning a signal to each measured intensity; and
processing the two measured intensity signals and assigning a signal to a respective point of an image of the material;
wherein spatially and/or temporarily concentrated laser light is used for illuminating the material and for causing two or more photon excitations in molecules of the sample.

11. The method of claim 4, further comprising: determining Stokes parameters (I,Q,U,V) of light from at least one of the illuminated points.

12. The method of claim 11, further comprising:
determining elements of a Mueller matrix ma transmitted laser beam of the microscope by changing the polarization state of the illuminating laser beam four steps while determining Stokes parameters (I,Q,U,V) in each of the said four states, the four steps comprising depolarized, linearly polarized at 0 or 90 degree, linearly polarized at +45 or −45 degree, and circularly polarized.

13. An apparatus for determining differential polarization quantities of a test material using a laser scanning microscope comprising:
a laser light source for generating a single beam, the single beam illuminating a test material;
a polarization state generator disposed between a the laser light source and a the material being tested for generating a beam of known and adjustable or variable polarization state;
a detector for determining the intensity of light with a polarization state modified by the material or intensity of light with a polarization state of light emitted by the material, the detector receiving said light;
a means for separating different polarization components in space or time disposed between the sample and the detector; and
a processing unit for processing the polarization components and for determining the differential polarization quantities of the sample.

14. The apparatus of claim 13, further comprising an optical component disposed in the light received from the material for dividing the polarization components in space according to polarization state thereof or according to a predetermined percentage of the intensity with the detector in the light beams divided according to the polarization state of the polarization components or with the detector and an analyzer in front of the detector for selectively transmitting one of the polarization components in the light beams divided according to the predetermined percentage of the intensity.

15. An apparatus for determining differential polarization quantities of a test material using a laser scanning microscope comprising:
a polarization state generator disposed between a laser light source and the material being tested;
a detector for determining the intensity of light with a polarization state modified by the material or intensity of light emitted by the material, the detector receiving said light;
a means for dividing polarization components in space or dine disposed in front of the detector; and
a first polarization modulator in the light received from the material for dividing the polarization components in time; and
a passive polarization analyzer disposed in front of the detector.

16. The apparatus of claim 15, further comprising:
at least one wavelength selective beam splitter disposed between the passive polarization analyzer and detector; and
at least one detector disposed in the light beams divided by a wavelength selective beam splitter.

17. The apparatus of claim 13, further comprising a polarization state setting unit comprising a passive polarization optical component and a polarization modulator.

18. The apparatus of claim 13, further comprising a pin-hole aligned with the light received from the material for selecting a light component focused on the material.

19. An apparatus for determining the polarization properties of light emitted, reflected or transmitted by a material using a laser scanning microscope comprising:
a polarization state generator disposed between a laser light source and a material being tested,
a detector for determining intensity of light with a polarization state modified by the material or intensity of light emitted by the material, the detector receiving said light;
a means for dividing polarization components in space or time disposed in front of the detector; and
the laser light Source with spatially and/or temporarily concentrated laser light for at least two photon excitation of molecules of the material.

20. The apparatus of claim 15, further comprising a second polarization modulator disposed between the first polarization modulator and the passive polarization analyzer, with the second polarization modulator having an optical axis rotated by 45° relative to an optical axis of the first polarization modulator.

21. The apparatus of claim 20, wherein the polarization state generator comprises at least one of a depolarizer, a linear polarizer, and a circular polarizer and an optical phase retarder.

22. The apparatus of claim 13, further comprising:

a polarization state setting unit comprising a photoelastic modulator positioned between two passive linear polarizers each having a polarization plane, the polarization planes being parallel or perpendicular to each other and the optical axis of the photoelastic modulator being set at 45° relative to the passive linear polarizers; and a depolarizer disposed behind the second passive linear polarizer.

23. The apparatus of claim 13, further comprising a signal processing unit connected to an output of the detector.

24. The apparatus of claim 22, wherein the processing unit comprises at least one phase sensitive amplifier, a low-pass filter, an analog-digital converter and a digital-analog converter.

25. An apparatus for determining the differential polarization quantities, including the fluorescence detected linear and circular dichroism (FDLD, FDCD) of anisotropically absorbing test materials using a laser scanning microscope with a polarization state generator comprising:

a passive polarization optical component and a polarization modulator between a laser light source and a sample for generating polarized laser light with modulated polarization state sweeping between orthogonal polarization states, wherein a detector for determining the intensity of light emitted by the sample associated with polarization components of light illuminating said sample is positioned in the light emitted by the sample.

26. The apparatus of claim 13, further comprising:

a first polarization modulator in the light received from the material for dividing the polarization components in time; and a passive polarization analyzer disposed in front of the detector.

27. The apparatus of claim 26, further comprising:

at least one wavelength selective beam splitter disposed between the passive polarization analyzer and detector; and at least one detector disposed in the light beams divided by the wavelength selective beam splitter.

28. The apparatus of claim 26, further comprising a second polarization modulator disposed between the first polarization modulator and the passive polarization analyzer, with the second polarization modulator having an optical axis rotated by 45° relative to an optical axis of the first polarization modulator.

29. The apparatus of claim 28, wherein the polarization state generator comprises at least one of a depolarizer, a linear polarizer, and a circular polarizer and an optical phase retarder.

* * * * *